(12) United States Patent
Jackson

(10) Patent No.: US 6,443,989 B1
(45) Date of Patent: Sep. 3, 2002

(54) POSTERIOR EXPANDABLE FUSION CAGE

(76) Inventor: Roger P. Jackson, 6600 Indian La., Mission Hills, KS (US) 66208

( * ) Notice: Subject to any disclaimer, the term of this patent is extended or adjusted under 35 U.S.C. 154(b) by 0 days.

(21) Appl. No.: 09/729,398

(22) Filed: Dec. 4, 2000

(51) Int. Cl.[7] .................................................. A61F 2/44
(52) U.S. Cl. ..................................... 623/17.15; 606/61
(58) Field of Search .......................... 623/17.11, 17.12, 623/17.13, 17.14, 17.15, 17.16; 606/72, 73, 60, 61

(56) References Cited

U.S. PATENT DOCUMENTS

| | | | |
|---|---|---|---|
| 4,013,071 A | * | 3/1977 | Rosenberg ................ 128/92 B |
| 4,863,476 A | | 9/1989 | Shepperd |
| 5,554,191 A | | 9/1996 | Lahille et al. |
| 5,653,763 A | | 8/1997 | Errico et al. |
| 5,665,122 A | | 9/1997 | Kambin |
| 5,702,453 A | | 12/1997 | Rabbe et al. |
| 5,776,197 A | | 7/1998 | Rabbe et al. |
| 6,102,950 A | | 8/2000 | Vaccaro |
| 6,117,174 A | | 9/2000 | Nolan |
| 6,129,763 A | * | 10/2000 | Chauvin et al. .............. 623/17 |
| 6,165,219 A | * | 12/2000 | Kohrs et al. ............. 623/17.11 |

* cited by examiner

*Primary Examiner*—David J. Isabella
*Assistant Examiner*—Urmi Chattopadhyay
(74) *Attorney, Agent, or Firm*—John C. McMahon

(57) ABSTRACT

An interbody device for use between a pair of adjacent vertebrae includes a body and at least one expansion member. The body has upper and lower walls that are joined by a rear wall that functions as a spring hinge. The walls have anterior or distal ends that are supported in a non-expanded configuration by spaced feet that project out from the walls. The expansion member is elongate and has a threaded portion that is threadably received in the rear wall. Each expansion member also includes a head having an anterior wedge portion that engages the anterior ends of the walls and forces the walls apart as the expansion member is screwed into the body. A surface engages the expansion member after expansion and supports the walls during usage. Preferably, the expansion member is only one of a plurality of expansion members found in a kit which vary with respect to the diameter of the head thereof.

16 Claims, 4 Drawing Sheets

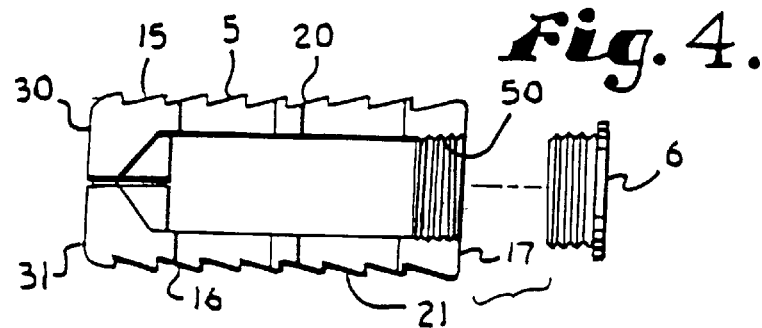
Fig. 4.
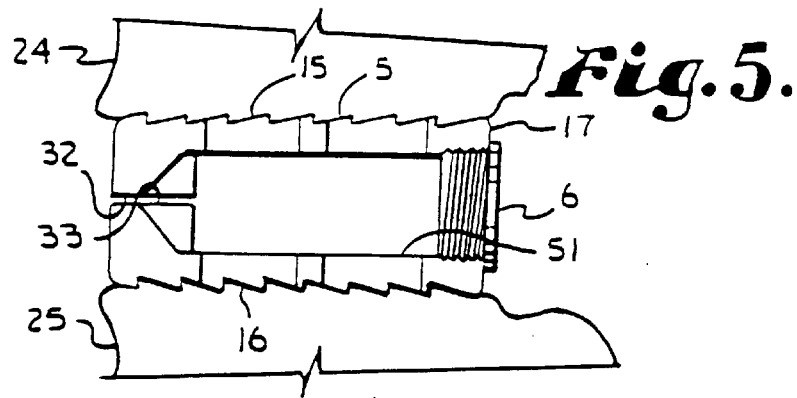
Fig. 5.
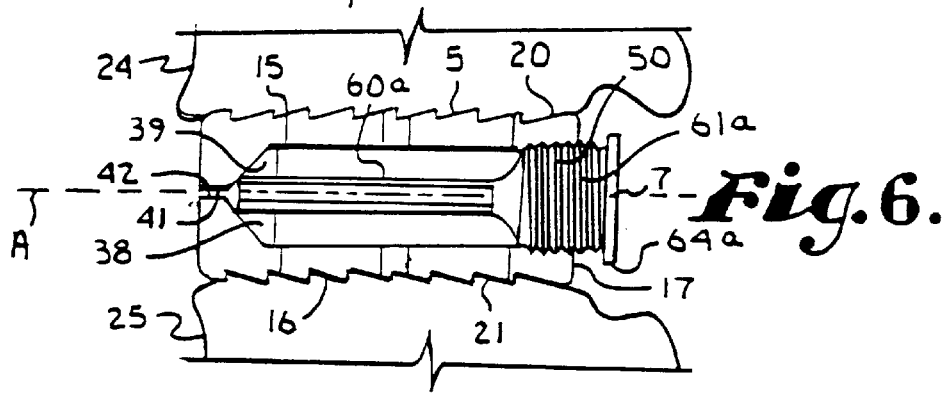
Fig. 6.
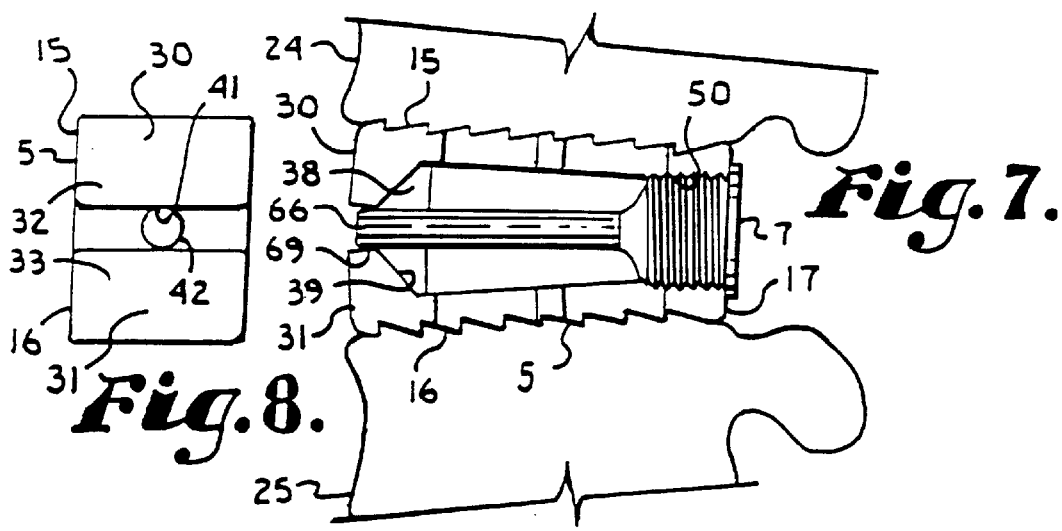
Fig. 7.
Fig. 8.

POSTERIOR EXPANDABLE FUSION CAGE

BACKGROUND OF THE INVENTION

The present application is directed to an expandable interbody device which is inserted from a posterior approach between adjacent vertebrae in the spine of a patient and which is also selectively anteriorly expandable.

Fusion cages, as well as other related interbody devices, are frequently utilized in spinal surgery between vertebrae of a patient. In particular, one or a pair of interbody devices are placed between the vertebrae to provide support and promote fusion between vertebrae where such is necessary due to disease, injury, general deterioration or a congenital problem.

Frequently, the anterior sides or fronts of the vertebrae also require additional spacing in comparison to posterior sides to correct curvature of the spine. Therefore, it is often desirable to use an anteriorly expandable interbody device so that the vertebrae are spread or spaced more on the anterior sides thereof than on the posterior sides thereof. It is seldom if ever desirable to space the posterior sides of the vertebrae more than the anterior sides thereof. Interbody devices which provide for anterior greater expansion are generally referred to as interbody expansion devices or expansion fusion cages. They are specifically expandable on the anterior end thereof such that the fronts of the adjacent vertebrae are more greatly spaced than the rears.

It is noted that interbody devices, such as fusion cages, may be inserted into the intervertebral space anteriorly or posteriorly. That is, in some instances the surgery is performed from the front and sometimes from the rear of the patient. The present application is directed to types of devices that are inserted posteriorly or from the rear of the patient and are generally referred to as posterior interbody devices or posterior fusion cages.

Interbody devices typically must be very strong along the entire length of the top and bottom walls of the device that engage the vertebrae. In particular, in the turning and twisting of everyday life, substantial forces can be exerted against the interbody devices and, in particular, against the anterior end thereof. This is even more so when the devices are subjected to unusual forces during an accident or the like. Some types of interbody devices in the prior art have provided for anterior expansion, but have not well supported the anterior end of the upper and lower walls. Such prior art devices have provided some kind of a wedge or rod that is urged rearward along a ramp of the device in such a way as to expand the anterior portion subsequent to it being placed between the vertebrae. Because the wedge moves rearwardly or posteriorly toward the back wall of the device in order to spread the walls, a lever arm of unsupported wall is formed between the front edge of each wall and the position where the wedge engages the walls. Substantial forces can act on this lever arm. The interbody devices poorly supported along the unsupported wall can fail due to forces exerted along the lever arm in the region.

Secondly, it is desirable for the interbody devices to not expand sideways, while the devices are expanding vertically. This need arises because it is often necessary to put interbody devices in close proximity to one another in side by side relationship. Sideways expansion may prevent desirable positioning of the interbody devices and may also interfere with positioning of bone chips for grafting between the interbody devices. Some prior art devices expand radially which expands the devices vertically, but also sideways.

When installing interbody devices, such as fusion cages, a surgeon may also find that it is necessary to have more anterior expansion than was initially anticipated in order to correct spinal curvature. Consequently, it is often desirable to be able to increase the expansion in increments that allow the surgeon to determine whether expansion is sufficient after each incremental advance in expansion and then further increase the expansion, if necessary. Therefore, it is desirable to have a kit that provides for alternative expansion devices, especially where such modular expansion devices can each be screwed into and secured in place in the cage so as to resist inadvertent removal during use.

Interbody devices, such as fusion cages, are quite expensive to produce in general. This is because the body of the devices must be made to very high tolerances in order to provide reproducible results and to provide the strength necessary to support the spine of the person. Because the surgeon is not always certain exactly which expansion size interbody device will be required until the surgery site is opened, it has been necessary for the surgeon to have on hand many different sizes of fusion cages and, in some cases, different types of fusion cages, such as expandable and non-expandable, so as to insure that the necessary item will be present when the surgery is performed.

Consequently, it is also desirable to be able to provide an interbody device that is modular in nature and easily adjusted to many degrees of expansion and that it may be used as efficiently with no expansion as with expansion, so that the same body can be used with different degrees of expansion. Many of the expandable types of prior art fusion cages cannot be used as non-expandable type cages.

Further, it is desirable for a single fusion cage body to be utilized for virtually any degree of expansion desired or foreseeable by simply providing a set of comparatively much less expensive expansion members in a kit, any of which expansion members may be used in conjunction with the body to provide for various and different degrees of expansion and each of which may be removed after insertion into a fusion cage body and replaced with a different expansion member without removing the cage body from between vertebrae.

SUMMARY OF THE INVENTION

A posterior interbody device or fusion cage for use between a pair of adjacent vertebrae in order to provide support and/or promote growth between the vertebrae that have been destabilized due to injury, illness or the like. The interbody device includes a body which may be rectangular in shape in which case the device is slid or driven between the vertebrae or generally cylindrical in shape and often threaded, in which case the device is screwed between the vertebrae. The body has an upper wall and a lower wall that are connected by a rear or posterior wall in a somewhat U-shaped configuration. The body is hinged about the rear wall by utilization of a material of construction that is flexible, such as stainless steel or titanium, so that the rear wall functions like a spring in conjunction with the upper and lower walls, so that the upper and lower walls are able to pivot relative to each other at the rear, when a spreading force is applied to the walls, which causes the anterior ends of the upper and lower walls rotate from an initial non-expanded configuration anteriorly to an expanded configuration anteriorly. In particular, the upper and lower walls are initially in a non-expanded state wherein the upper and lower walls are generally parallel and subsequently may be expanded by a plurality of expansion members to various expanded states wherein the upper and lower walls are at angles relative to each other which angles increase with expansion.

The upper and lower walls also have legs on either side of the anterior end thereof that face toward similarly positioned legs on the other wall and which abut against each other when the device is in the non-expanded configuration thereof, so the cage can be utilized operably in a non-expanded configuration. An aperture is formed between the legs and preferably extends through the body in such a manner as to form an interior chamber suitable for receiving bone chips or other growth promoting media. The body also preferably has upper and lower windows which communicate with the chamber and open onto the surface of the vertebrae, when in use, so as to promote growth of bone through the interbody device. The rear wall of the body includes a threaded bore.

An expansion member, preferably having a shape similar to a large headed bolt, is utilized to apply spreading force to the upper and lower walls so as to expand the body anterior end. The expansion member includes an elongate shaft having a rear portion threaded so as to be operably and threadably received in the rear wall bore and has a head at an opposite end. The shank includes a stop, preferably adjacent the threaded rear portion abutting the rear wall and being of enlarged diameter compared to and adjacent to the threaded rear portion, which insures that the expansion member is properly positioned during use.

The expansion member head varies in diameter depending on the expansion desired. The expansion head is sized, and shaped in position so as to engage a wedge mating or ramp surface located anteriorly on facing surfaces of each of the lower and upper walls. In particular, the expansion head first engages the mating surfaces on the walls near the posterior end of the ramp surface and then the mating surface slides along the ramp surface as the expansion member is screwed into the rear wall bore. Alternatively, the ramp may be associated with the wall and the expansion member then has an edge or surface that mates with and slides along such a ramp in the wall. In this manner the anterior end of the body is forced to spread or space vertically until a forward or anterior end of the ramp surface is reached. The ramp surface is adjacent to a support surface that is generally parallel to an axis of rotation of the expansion member and transfers the support of the upper and lower walls to the support surface as the expansion member is further rotated clockwise and advanced into the rear wall bore. Continued advancement of the expansion member to the stop causes the head to pass between the anterior ends of the upper and lower walls and to be fully supported by opposed surfaces to thereafter provide support to the upper and lower walls at the anterior ends thereof and keep the upper and lower walls in a preselected spaced relationship relative to each other.

Finally, in use each interbody device is normally provided with a set or kit of expansion members wherein each member of the set provides a different degree of spacing of the anterior end of the interbody device, for example, with one half or one millimeter differences in spacing between each size. In this manner, a surgeon can utilize the interbody device without an expansion member or can alternatively select from a number of expansion members with different sized heads to provide appropriate expansion of the anterior end of the interbody device. Normally, the surgeon would start with no or minimal expansion and then increase incrementally toward greater expansions until the surgeon is satisfied with the expansion provided.

OBJECTS AND ADVANTAGES OF THE INVENTION

Therefore, the objects of the present invention are: to provide a posterior interbody device or fusion cage for use between a pair of vertebrae that is expandable; to provide such an interbody device that has a body and at least one expansion member wherein the expansion member includes a head that engages an anterior portion of upper and lower walls of the body so as to spread the body from the anterior end thereof; to provide such a device wherein a single body may be utilized either without an expansion member or in conjunction with any of an alternative group of modular expansion members, each producing a different degree of expansion and contained in a kit of expansion members; to provide such a device wherein an expansion member that produces one degree of expansion can be screwed into the body such that the body expands and thereafter the expansion member can be removed and another expansion member producing a greater degree of expansion can be subsequently inserted; to provide such a device wherein the expansion members include an anterior or frontward head that rests on opposed anterior surfaces of the upper and lower body walls subsequent to full insertion of the expansion member; to provide such a device wherein the device expands vertically and not horizontally or side to side; to provide such a device including a central cavity and windows to allow for packing with bone chips or other growth media so as to promote fusion between adjacent vertebrae exposed to the windows; to provide such a device wherein a single body may be alternatively utilized with a number of different expansion members, such that multiple different sized bodies are not required to be maintained in stock during a surgical operation; to provide such a device that does not cantilever the walls over a wedge that is medially located with respect to the body, but rather positions the expansion head, ramp surfaces and the support surfaces at or near the anterior end of the body at all times during expansion, so as to continuously provide support to anterior ends of the walls; and to provide such a device which is relatively inexpensive to produce, extremely easy to use and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 4 is a cross-sectional view of the body, taken along line 4—4 of FIG. 2, and a non expanding member.

FIG. 5 is a cross-sectional view of the body, similar to the view taken along line 4—4 of FIG. 2, with the non-expansion member inserted therein and located between two vertebrae.

FIG. 6 is a cross-sectional view of the body, similar to the view taken along line 4—4 of FIG. 2, with a first expansion member partially inserted therein prior to expansion and located between the vertebrae.

FIG. 7 is a cross-sectional view of the body, similar to the view taken along line 4—4 of FIG. 2, with the first expansion member fully inserted so that the body is expanded and located between the vertebrae.

FIG. 8 is a front elevational view of the body with the first expansion member fully inserted therein.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
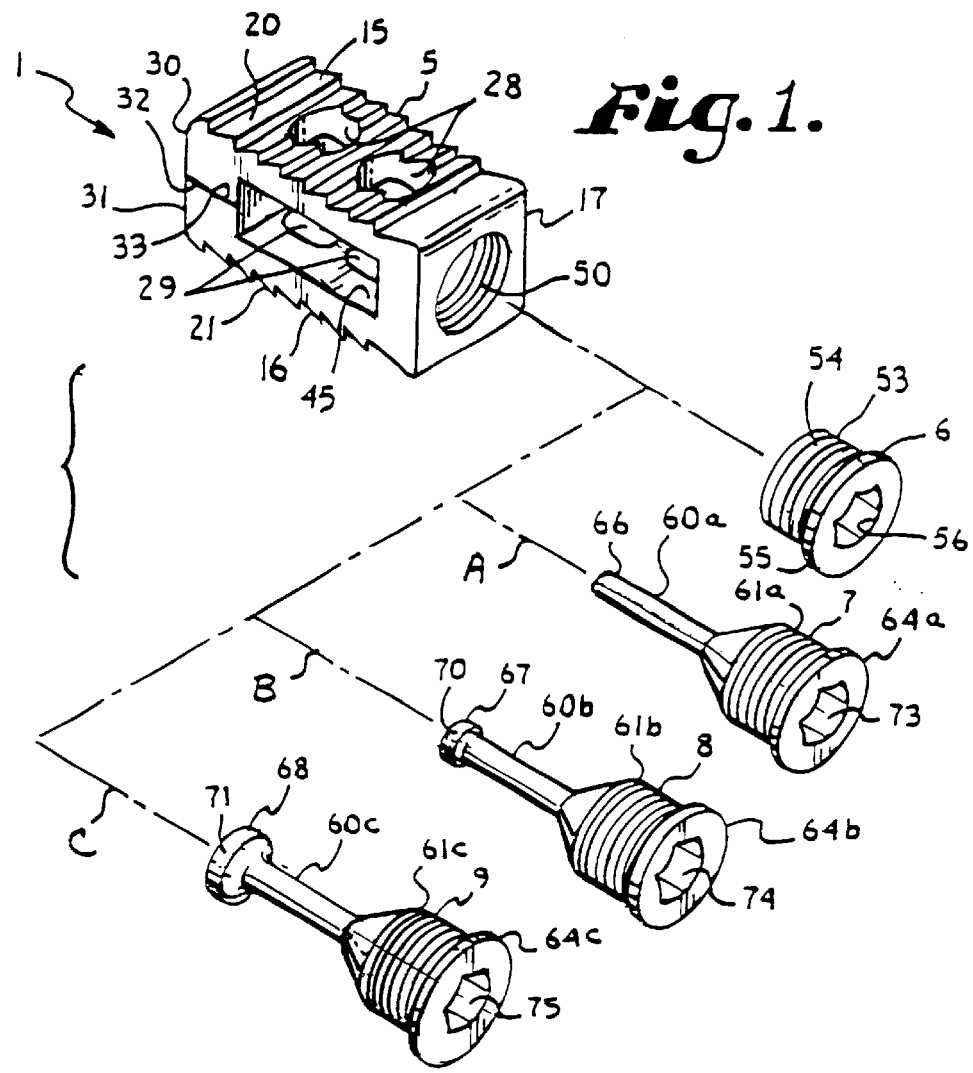
FIG. 1 is a perspective and exploded view of an expandable, posteriorly inserted interbody fusion device, illustrating a body of the device in a non-expanded configuration and a plurality of alternative expansion members.
Figure 2:
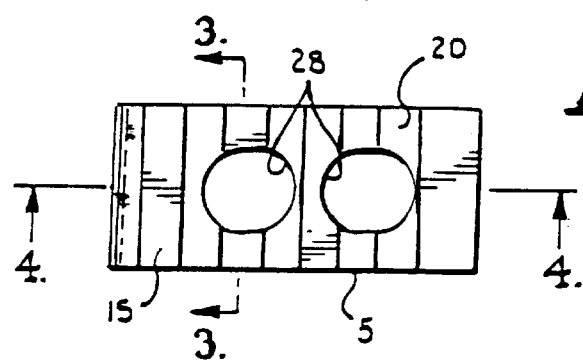
FIG. 2 is a top plan view of the body in the non-expanded configuration.

The reference numeral 1 generally designates an interbody device or fusion cage in accordance with the present invention having a body 5. The device 1 also includes a non-expansion member 6 and a set of expansion members, including expansion members 7, 8 and 9. The non-expansion member 6 and the expansion members 7, 8 and 9 are used individually and interchangeably or modularly in the body 5, but only one at a time. The expansion member 9 is the largest of the set and is seen in FIG. 1. The expansion member 7 is the smallest of the group and is seen in FIG. 6. Each expansion member 7, 8 and 9 has an axis of rotation A, B and C respectively, as seen in FIG. 1. Although only three expansion members are shown in the present embodiment and together with the body 5 and non-expansion member 6 form a kit for use in spinal surgery, it is foreseen that a much larger group of expansion members, each having a different head diameter, could be included in the kit with smaller size increments between the size The body 5 includes a top or upper wall 15, a bottom or lower wall 16 and a posterior or rear wall 17. The upper wall 15 and lower wall 16 are joined near the posterior ends thereof to the rear wall 17. As used herein posterior and anterior pertain to configurations in the human body and posterior would be to the right in FIG. 4, while anterior would be to the left in FIG. 4. The upper wall 15 and lower wall 16 are initially in substantially parallel relationship to one another and are urged to retain that position or configuration by the springy or resilient nature of materials of construction thereof which maintain the non-expanded shape thereof unless force is applied to change that shape through expansion members 7, 8 or 9.

Preferably the body 5 is constructed of a bio-compatible metal, such as stainless steel or titanium or other material, and the rear wall acts as a spring to try to maintain the upper wall and lower wall 15 and 16 in parallel relationship while also functioning as a hinge, when the upper and lower walls 15 and 16 are anteriorly forced apart by application of spreading force to the walls 15 and 16.

The upper and lower walls 15 and 16 have bone engaging outer surfaces 20 and 21 respectively which are serrated in such a manner as to bite into the bone of vertebrae 24 and 25 respectively, after being placed therebetween. The upper and lower walls 15 and 16 also have fenestrations or windows 28 and 29 respectively. Although the present embodiment is shown with a pair of each of the windows 28 and 29, it is foreseen in some circumstances that no windows would be provided and in other circumstances different members of windows may be provided in the walls 15 and 16.

Figure 3:
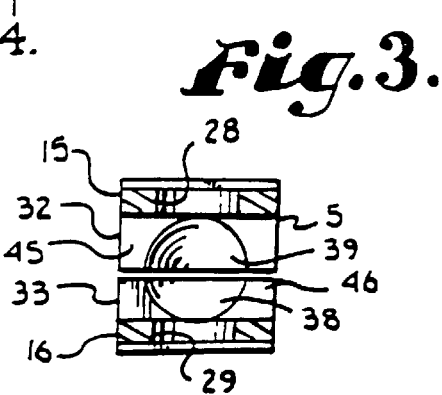
FIG. 3 is a cross-sectional view of the body, taken along line 3—3 of FIG. 2.
Figure 9:
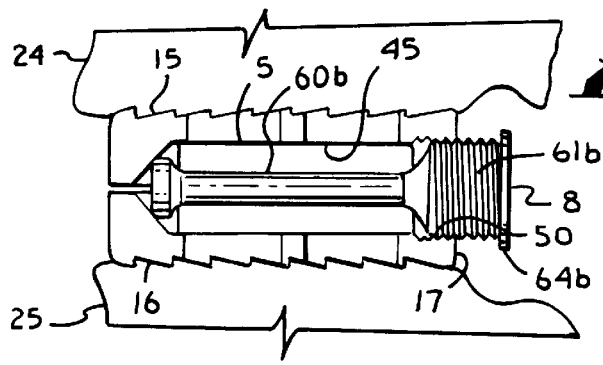
FIG. 9 is a cross-sectional view of the body similar to the view taken along line 4—4 of FIG. 2, with a second expansion member partially inserted therein prior to expansion and located between the vertebrae.

Near anterior ends 30 and 31 of each of the walls 15 and 16 are legs 32 and 33 respectively. The legs 32 and 33 of each of the walls 15 and 16 extend toward one another and abut or almost abut when the body 5 is in a non-expanded configuration thereof, such as is shown in FIG. 1, so as to maintain the non-expanded configuration of the walls 15 and 16 when a load is applied thereto. In this manner the front or anterior ends 30 and 31 of the walls 15 and 16 are supported by the legs 32 and 33 in the non-expanded configuration. Located on each wall 15 and 16 and located behind each leg 32 and 33 is a ramp 38 and 39 respectively which in the illustrated embodiment are mating surfaces for initially mating with or engaging expansion members 7, 8 or 9 selectively to bias apart the walls 15 and 16 during insertion of the expansion members 7, 8 or 9. Each ramp 38 and 39 has a semicircular cross-section (see FIG. 3) and slopes from the facing sides of walls 15 and 16 to facing support surfaces 41 and 42 on the facing sides of the legs 32 and 33. The support surfaces 41 and 42 shown in the illustrated embodiment are generally flat, but it is foreseen that the support surfaces could have a central depression or the like to help guide and stabilize the expansion member 7, 8 and 9. Immediately located along and between the walls 15 and 16 are a pair of side windows 45 and 46.

The rear wall 17 includes a centrally located threaded bore 50. A bone chip receiving cavity 51 is located between the walls 15, 16 and 17.

The non-expansion member 6 has a plug body 53 with a threaded outer surface 54 sized and shaped to be received in the threaded bore 50. The plug body 53 also has a rear flange 55 that is larger in diameter than the surface 54 and operably functions as a stop limiting penetration of the plug body relative to the threaded bore 50. Extending into the rear of the plug body 53 is a hexagonal shaped bore 56 sized and shaped to receive an Allen wrench tool or the like (not shown) for operably rotating and driving the non-expansion member 6 into the threaded bore 50.

Each of the expansion members 7, 8 and 9 include an elongate shank 60 having a threaded posterior portion 61 that is sized and shaped to be received in the rear wall threaded bore 50 and that is similar in size and shape to the plug body 53. In the illustrated embodiment the posterior portion 61 has a larger diameter than the remainder of the shank 60 which reduces the space occupied by the remainder of the shank 60, but both can be the same size in certain embodiments. Also the posterior portion 61 may have an axial extending opening to allow for inserting bone fragments into the body 5 through the posterior portion 61. Each shank 60 also has a stop 64 that is effectively a region of increased diameter located at the posterior end of the threaded posterior portion 61 thereof. The stops 64 insure that the expansion members 7, 8 and 9 will be properly positioned when fully installed. Each of the expansion members 7, 8 and 9 also include a head 66, 67 and 68 respectively.

The heads 66, 67, and 68 each include an outer cylindrical shaped surface 69, 70 and 71 respectively coaxially attached to the shank 60 thereof. During installation of the expansion members 7, 8 or 9 into the body 5, one of the cylindrical shaped surfaces 69, 70 or 71 as the case may be first engages the ramps 38 and 39 on the anterior ends of the walls 15 and 16. While the present embodiment surfaces 69, 70 and 71 have a forward edge, it is foreseen that an angled conical shaped surface could function for this purpose also in which case the ramps 38 and 39 could be more edge like in nature. The cylindrical surfaces 69, 70 or 71 ultimately engage and rest on the support surfaces 41 and 42.

Figure 10:
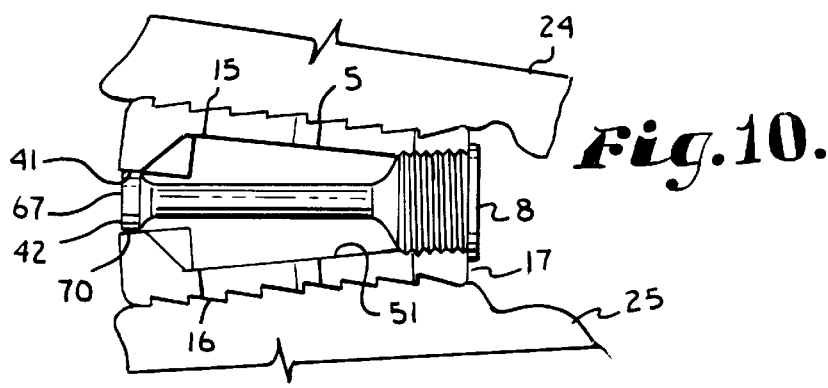
FIG. 10 is a cross-sectional view of the body similar to the view taken along line 4—4 of FIG. 2, with the second member fully inserted therein and located between the vertebrae.
Figure 11:
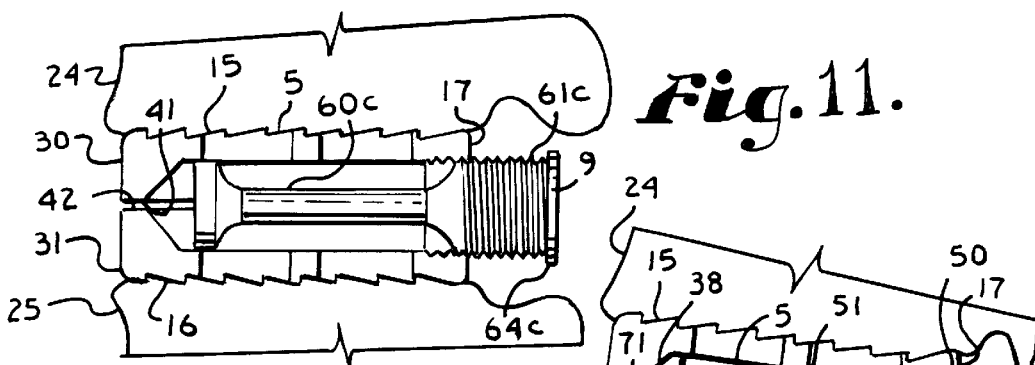
FIG. 11 is a cross-sectional view of the body similar to the view taken along line 4—4 of FIG. 2, with a third expansion member partially inserted therein prior to expansion and located between the vertebrae.
Figure 12:
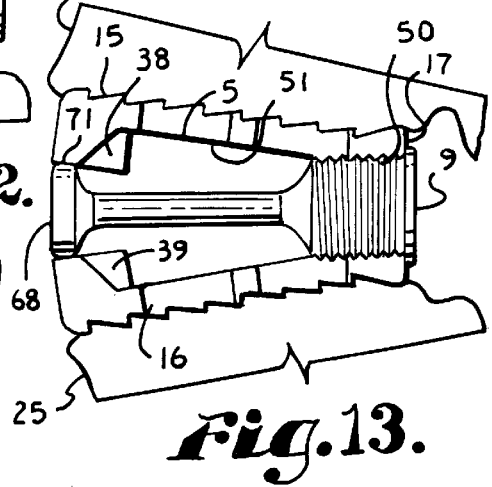
FIG. 12 is a cross-sectional view of the body similar to the view taken along line 4—4 of FIG. 2, with the third expansion member partially inserted therein with partial expansion of the body and located between the vertebrae.
Figure 13:
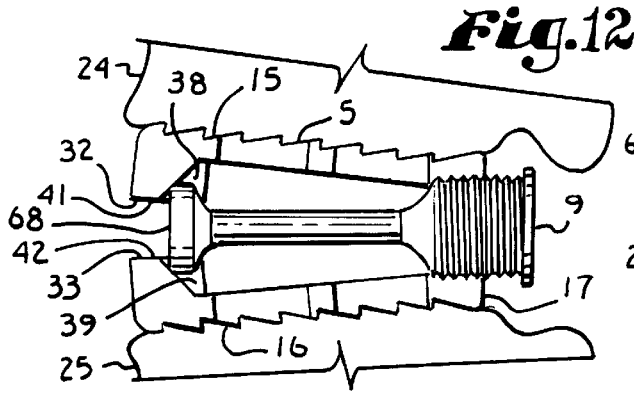
FIG. 13 is a cross-sectional view of the body similar to the view taken along line 4—4 of FIG. 2, with the third expansion member fully inserted such that the body is anteriorly expanded and located between the vertebrae.
Figure 14:
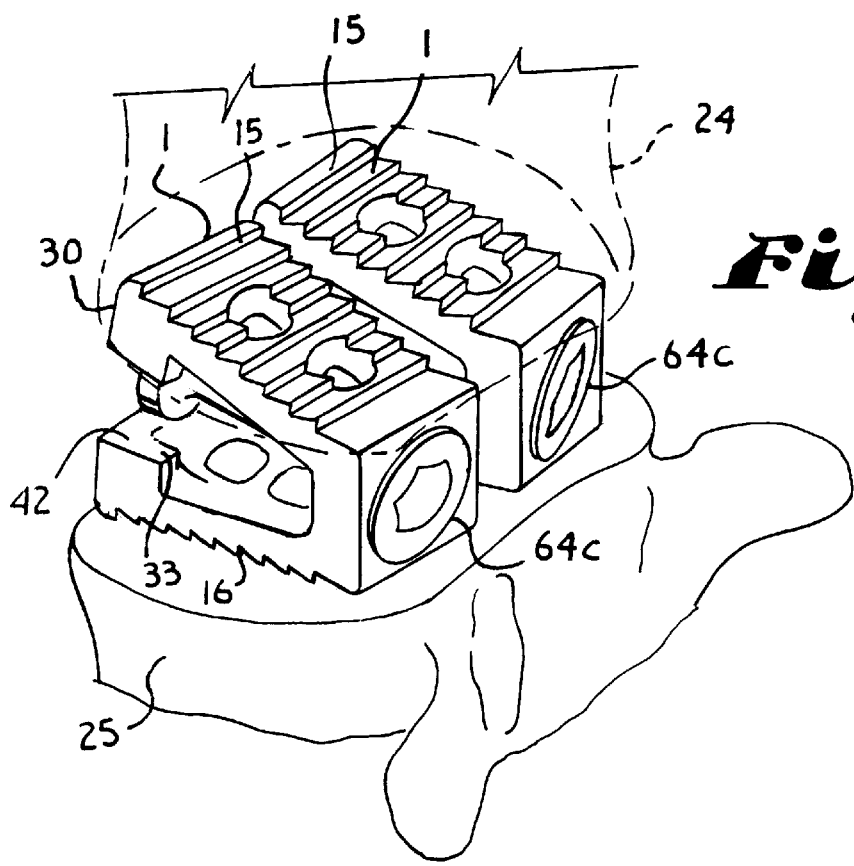
FIG. 14 is a perspective view of a pair of the fusion devices located between the vertebrae and being anteriorly expanded.
Figure 15:
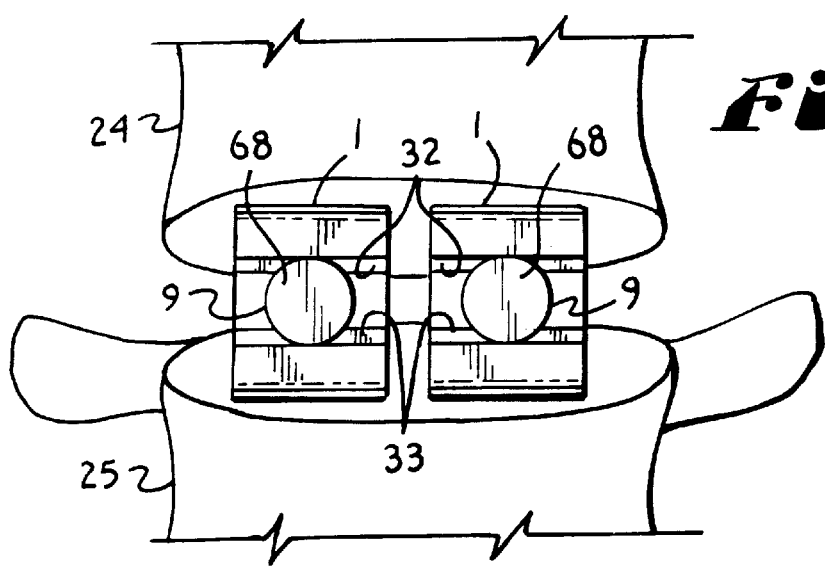
FIG. 15 is a fragmentary front elevation view of the pair of fusion cages shown in FIG. 14 located between a pair of vertebrae

As seen in FIG. 1, the heads 66, 67 and 68 of each of the expansion members 7, 8 and 9 increase progressively in diameter. In this manner the expansion members 7, 8 and 9 provide increasing expansion of the anterior ends 30 and 31 of the body 5, as is seen in FIGS. 7, 10 and 13 respectively, when fully inserted into the body 5. A hexagonal bore 73, 74 or 75 is provided in the rear of each of the members 7, 8 and 9 and is sized and shaped to mate with an Allen wrench driver for rotating and torquing the members 7, 8 and 9.

In use the pad or disc located between a pair of vertebrae 24 and 25 is removed or partially removed and a pair of the bodies 5 are inserted by a posterior approach between the vertebrae 24 and 25. Once the bodies 5 have been positioned between the vertebrae 24 and 25 the surgeon checks to determine whether additional anterior expansion is desirable. If additional expansion is desired, normally the expansion member having the smallest expansion head diameter, in this case expansion member 7, is inserted in each of the bodies 5 and screwed into place. As the members 7 are screwed inwardly, the heads 66 thereof engage the ramp surfaces 38 and 39 of the upper and lower walls 15 and 16 and space the anterior ends 30 and 31 of the upper and lower walls 15 and 16 respectively. The surgeon then determines whether or not additional anterior expansion is required. If further expansion is needed, the first expansion member 7 is removed from each of the bodies 5 and the second expansion member 8 of somewhat larger diameter is installed. This process is continued until the surgeon is satisfied that the proper expansion has been achieved. If no expansion is initially needed the non-expansion member 6 is installed in the bore 50.

It is to be understood that while certain forms of the present invention have been illustrated and described herein, it is not to be limited to the specific forms or arrangement of parts described and shown.

What is claimed and desired to be secured by letters patent is as follows:

1. A posterior interbody device that is anteriorly variably expandable; said device comprising:

a) a U-shaped body having an upper wall and a bottom wall hingeably joined by rear wall; said rear wall having a threaded bore, said upper and lower walls having a non-expanded configuration;

b) said upper and lower walls each having an anterior mating region that face each other;

c) an elongate expansion member; said expansion member being threaded and being operably threadedly received in said rear wall bore;

d) said expansion member having a wedge that is sized, shaped and positioned to engage said upper and lower anterior mating regions as said expansion member is threadedly advanced into said bore such that anterior ends of upper and lower walls are urged into an expanded configuration wherein said upper and lower walls become spaced greater than said non-expanded configuration.

2. The device according to claim 1 wherein:

a) said expansion member has an axis of rotation; and b) said wedge is cylindrical shaped and is coaxial with said axis of rotation.

3. The device according to claim 1 wherein:

a) said body includes a support surface adjacent and anterior of said mating region.

4. The device according to claim 1 wherein:

a) said expansion member has an axis of rotation;

b) said expansion member has a threaded region near a posterior end thereof that is screwable into a thread in said rear wall bore;

c) said expansion member has a head near an anterior end thereof; said head including said wedge in the shape of a cylinder; said body including a supporting surface anterior of said mating region that is sized, shaped and positioned to engage and support said upper and lower walls when said expansion member is fully inserted into said body; so that as said expansion member is threadedly advanced into said body, said wedge engages said upper and lower wall wedge mating regions and vertically spreads the anterior ends of said upper and lower walls while said walls hinge at a posterior end thereof and, thereafter said support surface engages and supports anterior ends of said upper and lower walls in a preselected anterior spaced configuration.

5. The device according to claim 4 wherein:

a) said expansion member includes a stop located to limit advancement of said expansion member into said body and to position said expansion member in said body.

6. The device according to claim 6 wherein:

a) said stop is adjacent and posterior to said threaded region of said expansion member and has a greater diameter than said threaded region.

7. The device according to claim 1 wherein:

a) said upper and lower walls each include a window positioned to allow growth of bone therethrough during usage.

8. The device according to claim 1 wherein:

a) said upper and lower walls have anterior surfaces that engage under load when in a non-expanded configuration such that said device is adapted to be utilized alternatively as an expanded or non-expanded fusion cage.

9. The device according to claim 1 wherein:

a) said upper and lower walls each include an anterior pair of spaced legs that respectively engage and rest against legs of the opposite wall when in the non-expanded configuration and when under a load that urges the legs toward one another.

10. The device according to claim 1 wherein:
   a) when fully inserted, said expansion member extends longitudinally through said body from a posterior end thereof in said threaded bore to near an anterior end thereof.

11. A posterior interbody device that is anteriorly variably expandable; said device comprising:
   a) a U-shaped body having an upper wall and a bottom wall hingeably joined by a rear wall; said rear wall having a threaded bore, said upper and lower walls having a non-expanded configuration;
   b) said upper and lower walls each having an anterior mating region that face each other;
   c) first and second elongate expansion members; each of said expansion member being threaded and being operably threadedly received in said rear wall bore;
   d) each of said expansion members having a wedge that is sized, shaped and positioned to engage said upper and lower anterior mating regions as a respective expansion member is threadedly advanced into said bore such that anterior ends of upper and lower walls are urged into an expanded configuration wherein said upper and lower walls become spaced greater than said non-expanded configuration;
   e) said body including a support surface adjacent to and anterior of said mating region; and
   f) including said first and second expansion members being incorporated in a set wherein said first and second expansion members have respective cylindrical surfaces of different diameters so that said first and second expansion members can be selectively individually used with said body to produce different degrees of expansion of the anterior end of said body.

12. A posterior interbody device that is anteriorly variably expandable; said device comprising:
   a) a U-shaped body having an upper wall and a bottom wall hingeably joined by a rear wall; said rear wall having a threaded bore, said upper and lower walls having a non-expanded configuration;
   b) said body being generally rectangular in cross section;
   c) said upper and lower walls each having an anterior mating region that face each other;
   d) an elongate expansion member; said expansion member being threaded and being operably threadedly received in said rear wall bore; and
   e) said expansion member having a wedge that is sized, shaped and positioned to engage said upper and lower anterior mating regions as said expansion member is threadedly advanced into said bore such that anterior ends of upper and lower walls are urged into an expanded configuration wherein said upper and lower walls become spaced greater than said non-expanded configuration.

13. In an expandable posterior interbody fusion cage; the improvement comprising:
   a) said cage having a U-shaped body having upper and lower walls each with anterior mating regions near an anterior end thereof; and
   b) an elongate expansion member that is threadedly received in said body; said expansion member having a head with an anterior wedge for operably engaging said body mating regions and expanding an anterior end of said cage as said expansion member advances into said body.

14. In a posterior expandable fusion cage having an expansion member; the improvement comprising:
   a) wherein said expansion member is a first expansion member and including in an expansion kit a second expansion member that is interchangeable with said first expansion member; each of said first and second expansion members being cooperatively mateable with said cage to provide a different degree of anterior expansion of said cage and operably producing a different degree of expansion in said fusion cage.

15. In a posterior expandable fusion cage having an expansion member; the improvement comprising:
   a) wherein said expansion member is a first expansion member and including in an expansion kit a second expansion member that is interchangeable with said first expansion member; each of said first and second expansion members being cooperatively mateable with said cage to provide a different degree of anterior expansion of said cage; and
   b) said kit including a non-expansion plug.

16. The cage according to claim 15 wherein:
   a) at least one of said non-expansion plug and expansion members includes a threaded region for being threaded into a bore in a rear wall of said cage and said threaded region includes a passageway therethrough to allow insertion of matrix material into said cage after installation of said one of said non-expansion plug and expansion members.

* * * * *